United States Patent [19]
Oliva

[11] Patent Number: 5,385,156
[45] Date of Patent: Jan. 31, 1995

[54] DIAGNOSTIC AND TREATMENT METHOD FOR CARDIAC RUPTURE AND APPARATUS FOR PERFORMING THE SAME

[75] Inventor: Philip B. Oliva, Boulder, Colo.

[73] Assignee: Rose Health Care Systems, Denver, Colo.

[21] Appl. No.: 113,293

[22] Filed: Aug. 27, 1993

[51] Int. Cl.⁶ .............................................. A61B 65/02
[52] U.S. Cl. ..................................... 128/898; 128/696
[58] Field of Search ............... 128/630, 669, 897, 898, 128/704, 696; 606/151; 623/1

[56] References Cited

U.S. PATENT DOCUMENTS

| | | | |
|---|---|---|---|
| 3,272,204 | 3/1961 | Artandi et al. | 606/151 |
| 4,693,720 | 9/1987 | Scharnberg et al. | 623/66 |
| 4,983,184 | 1/1991 | Steinemann | 623/66 |
| 5,100,422 | 3/1992 | Berguer et al. | 606/151 |
| 5,148,812 | 9/1992 | Verrier et al. | 128/704 |
| 5,201,745 | 4/1993 | Tayot et al. | 606/151 |
| 5,213,106 | 5/1993 | Lerner | 128/704 X |

FOREIGN PATENT DOCUMENTS

1194391  11/1985  U.S.S.R. .................. 128/696

Primary Examiner—Lee S. Cohen
Assistant Examiner—Samuel Gilbert
Attorney, Agent, or Firm—Beaton & Folsom

[57] ABSTRACT

A method for diagnosing and treating anticipated cardiac rupture and an apparatus for the same. Anticipated cardiac rupture is diagnosed by examining one or more of several predictive symptoms, including pericarditis, repetitive unprovoked emesis, restlessness and agitation, abnormal ECG ST segments and T waves, and abrupt hypotension and bradycardia. The treatment includes the adhesion of a mesh patch to the myocardium by introducing the patch into the pericardia sac through an endoscope, applying the patch to the myocardium using a pair of graspers, and adhering the patch to the myocardium by applying a cyanoacrylate glue to the patch.

9 Claims, 3 Drawing Sheets

DIAGNOSTIC AND TREATMENT METHOD FOR CARDIAC RUPTURE AND APPARATUS FOR PERFORMING THE SAME

FIELD OF THE INVENTION

The present invention relates to the field of cardiac rupture and, in particular, to a method of anticipating cardiac rupture, and to a treatment method for preventing cardiac rupture and an apparatus used with the treatment.

BACKGROUND OF THE INVENTION

Cardiac rupture refers to a rupture of the left ventricle of the heart, generally following an acute myocardial infarction. If untreated, the condition usually is fatal immediately or within a few days depending on the extent of the rupture. It is believed that such rupture occurs in approximately 10% of patients with fatal acute myocardial infarction. Bates, RJ., Beutler, S., Resnekov, L., Anagostopoulos, CE. Cardiac Rupture—Challenge in Diagnosis and Management. Am. J. Cardiol. 1977; 40:429-37. It causes 25,000 deaths a year in the United States alone and is the second most common cause of the death after an acute myocardial infarction.

Cardiac rupture has been considered essentially unpredictable, although occasionally a symptom or sign has been reported at or just before the time of rupture. The rupture has also been generally considered untreatable, although recently methods have been described involving suture and sutureless repair with a patch after opening the pericardium. See, Subacute Cardiac Rupture: Repair with a Sutureless Technique, J. M. Padro, et al., Ann. Thorac. Surg. 1993; 55:20-4.

Stated another way, until the present invention, cardiac rupture could not be reliably anticipated, and there was no real treatment for it after it occurred other than by highly invasive procedures involving opening the pericardium. Patients who experienced cardiac rupture usually died, either immediately before any treatment could be administered or within several days due to the present treatment methods not yet being widely accepted. A few fortunate patients lived long enough to be treated and were under the care of physicians acquainted with the new treatment methods. Even those few, however, had to undergo a major surgical procedure that was both highly invasive and somewhat experimental.

SUMMARY OF THE INVENTION

The present invention includes (1) a method for anticipating cardiac rupture based on several predictive symptoms, (2) a method for treatment to prevent cardiac rupture in those patients in which it is anticipated, and (3) an apparatus for performing the treatment method.

The predictive symptoms occur much more often in patients with rupture than in those who do not develop that complication. Pericarditis is the most common but least specific symptom portending rupture, whereas repetitive, unproved emesis more than 24 hours after admission and restlessness and agitation are much more specific, occurring very infrequently in patients without rupture. Moreover, all patients with rupture tend to have at least one premonitory symptom and in most patients, two or more of the triad exist, whereas very few patients without rupture have two or three symptoms. Thus, several symptoms often occur a few hours to several days before rupture and convey a high predictive value.

In addition, deviation of the ST segment or T wave, or both, from the usual evolutionary pattern after acute myocardial infarction is observed in cases of rupture. After acute infarction, evolutionary ST-T wave changes normally occur in a characteristic and predictable pattern. The initial ST segment elevation of 1 to 5 mm or more recedes to 0 to 3 mm within 24 to 48 hours and should not recur in the absence of reinfarction, pericarditis or ventricular aneurysm. The T wave becomes inverted within 24 to 72 hours, with maximal T wave negativity always developing in the lead or leads displaying the maximal ST segment elevation initially. In contrast, among patients destined to sustain rupture, persistent, progressive or recurrent ST segment elevation often develops during the first 48 to 72 hours in patients who will sustain cardiac rupture but usually does not develop in patients who will not incur this fatal complication.

A departure of the T wave from the customary course is even more frequent among patients who will sustain cardiac rupture. T wave changes consist of persistently positive deflections after 48 to 72 hours or gradual reversal of initially inverted T waves. The region in which the T wave does not invert, or in which reversal of initially inverted T waves occurs, consistently corresponds with the subsequent site of rupture, often the midlateral or basal-lateral wall.

The most dramatic indicator of impending fatal rupture may be the development of abrupt hypotension and bradycardia, often with cyanosis and loss of consciousness. The bradycardia is mild (sometimes only relative), never due to atrioventricular block and consistently respond quickly to atropine.

Once an impending cardiac rupture is diagnosed, the condition can be treated by the surgical technique described herein. A trocar is used to introduce and advance a flexible fiber-optic device to the parietal pericardium. In a preferred embodiment, the fiber-optic device has a plurality of channels including at least one light source channel, an object lens, a large instrument channel, a small instrument channel, an air insufflation channel and an air desufflation channel.

The device has a flexible body and a position controllable tip that can be remotely manipulated from outside the patient in the manner of an ordinary gastroendoscope. An incision is made in the pericardial sac using scissors inserted through one of the instrument channels, and the tip of the device is advanced through the pericardial sac to within a few millimeters of the site of the impending or existing rupture site. The surface of the infarcted myocardium at the site of the impending or actual rupture is then dried by blowing air through the air insufflation channel while simultaneously removing air from the air desufflation channel. Such a drying method avoids suctioning and/or applying a sponge, gauze pad or similar material to the surface of the heart which could further damage the site of the impending or actual early rupture.

A rolled porous patch (such as MARLEX brand by Baird) wrapped around a grasper is introduced through the large instrument channel. The patch unfurls as it exits the large instrument channel upon entry into the pericardial sac. Another grasper is introduced through the small instrument channel, and the two graspers are used to facilitate the unfurling of the patch and to position the unfurled patch over the infarcted myocardium at the site of the impending or actual rupture. To facilitate the unfurling of the patch and to assist in the exact placement of the patch, a small amount of insufflation is delivered to the local area around the patch. The area is then dried again by simultaneous application of air and removal of air through the air insufflation channel and air desufflation channel.

The grasper is then removed from the large instrument channel, and a catheter is introduced having a syringe on the exterior end. The syringe is preloaded with a cyanoacrylate glue. The glue is injected through the catheter by the syringe and hardens onto the patch within a few seconds. The tip of the catheter is then used to apply mild pressure to the patch to allow very close approximation of the patch with the surface of the heart. The entire device is then withdrawn from the patient, and replaced with a chest tube of the same diameter. The chest tube is later withdrawn if no significant myocardial bleeding is observed within about 48 hours.

BRIEF DESCRIPTION OF THE DRAWINGS

FIGS. 4, 4A, 4B and 4C show an apparatus of the present invention, in which FIGS. 4A, 4B and 4C are details.

DETAILED DESCRIPTION OF THE INVENTION

First described is the novel diagnostic method of the present invention and then described is the treatment method including the novel apparatus used to accomplish that treatment.

DIAGNOSTIC METHOD EXAMPLE

Patients

The study group comprised 70 consecutive patients with autopsy or surgically proved rupture of the left ventricular free wall who survived at least 48 hours after the onset of an acute myocardial infarction and were cared for at two institutions over a 20-year period.

Clinical records, autopsy findings (68 patients) and surgical observations (2 patients) were reviewed. The data were collected retrospectively (64 patients) and prospectively (6 patients). The clinical information was derived by reviewing in detail the medical records of every patient. The temporal relation of the clinical events to each other and to the time of rupture was established.

Electrocardiograms

All patients initially had $\geq 2$ mm ST segment elevation in two or more contiguous precordial leads or $\geq 1$ mm ST elevation in two or more contiguous limb leads, utilizing the Fumagalli hexaxial system. See, Fumagalli, B. Unipolar Value of Standard Limb Leads: Lead VR and Rationale Arrangement of Limb Leads. Am. Heart J. 1954; 48:204-23. Criteria for the ECG site of infarction were adapted from the standardized terminology proposed by Surawicz et al. See, Surawicz, B., Uhley, H., Borun, R., et al. Task Force 1: Standardization of Terminology and Interpretation. Am. J. Cardiol. 1978; 41:130-45. A diagnosis of septal infarction was made when these changes appeared in leads $V_1$ to $V_2$, anterior infarction when in leads $V_3$ to $V_4$ and inferior infarction when in leads II, III and a VG. Anterolateral and inferolateral infarctions were diagnosed when these abnormalities also appeared in leads $V_5$ and $V_6$, and a superior (high lateral) infarction was diagnosed when these changes were present in leads I and aVL. A provisional diagnosis of posterior infarction was made when the initial ECG showed horizontal ST segment depression with a totally or terminally upright T wave in leads $V_1$ to $V_3$, as described by Boden et al. (see, Boden, WE., Kleiger, RE., Gibson, RS., et al., and the Diltiazem Reinfarction Study Group. Electrocardiographic Evolution of Posterior Infarction: Importance of Early Precordial ST-segment Depression. Am. J. Cardiol. 1987; 59:782-7), and confirmed when subsequent ECGs disclosed prominent primary R waves in leads $V_1$ to $V_3$ (R/S ratio $\geq 1$) with upright T waves.

The serial ECGs of each patient were independently reviewed by two observers to determine the pattern of evolution of the ST segment and T wave with special attention was given to their direction, magnitude and configuration.

Pathology

Pathologic observations were made at autopsy in 68 patients and at the time of surgery in the most recent two patients. The left ventricular mass covered by epicardium was divided for topographic purposes into three walls containing nine segments, as defined by Edwards et al.: the anterior wall (from the anterior interventricular groove to the anterior edge of the anterolateral papillary muscle), the lateral wall (from the anterior edge of the anterolateral papillary muscle to a line midway between two papillary muscles) and the inferior wall (from the aforementioned line to the posterior interventricular groove). See, Edwards, WD., Tajik, AJ., Seward, JB. Standardized Nomenclature and Anatomic Basis for Regional Tomographic Analysis of the Heart. Mayo Clin. Proc. 1981; 56:479-97. Each ventricular free wall was then divided into an apical, middle (mid) and basal third, yielding nine segments. The segment involved in the transmural tear was identified and the site of rupture designated accordingly.

Comparison Group

To evaluate the sensitivity, specificity and predictive value of the clinical events and ECG changes observed in the patients with rupture, the records of 100 consecutive patients with acute transmural myocardial infarction who did not sustain rupture were reviewed. A diagnosis of acute transmural myocardial infarction was made when chest pain accompanied by initial ST segment elevation was succeeded by the development of new or $\geq 0.04$-s Q waves—cognizant of the fact that Q waves are not synonymous with transmurality—or an R/S ratio $\geq 1$ in leads $V_1$ to $V_3$ and associated with an increase in the myocardial component of creatine kinase (CK-MB) within 6 to 30 hours after the onset of symptoms and a return to normal within 3 to 4 days. All ECGs of each patient were analyzed in blinded manner to ascertain the evolutionary pattern of the ST segment and T wave.

Definitions

A diagnosis of pericarditis was made if pleuritic or positional chest, left shoulder or scapular pain or a pericardial friction rub, alone or in combination, occurred during the first week after acute myocardial infarction and was not associated with reelevation of CK-MB levels. Abrupt hypotension was defined as the sudden reduction of systolic pressure to <90 mm Hg. Absolute bradycardia was defined as a heart rate of <60 beats/min and relative bradycardia was a heart rate of 60 to 90 beats/min but at least 30 beats/min less than the immediately preceding heart rate in conjunction with abrupt hypotension. The expected pattern of T wave evolution, as observed in the comparison group, was defined as a maximal T wave negativity of $\geq 3$ mm within 48 hours after infarction in the presence of reperfusion or $\leq 2$ mm within 72 hours in the absence of reperfusion (see later and FIG. 1A).

Statistical analysis. Comparisons of discrete variables were made using the chi-square test with the Yates correction. A p value <0.05 was considered statistically significant. All data are presented as mean value $\pm 1$ SD.

Clinical Characteristics

Clinical data on those patients who died of rupture are recorded in Table 1. There were 47 men and 23 women, ranging in age from 51 to 88 years. Previous hypotension, infarction and congestive heart failure were present in 65%, 18% and 3% of patients, respectively. In 31 patients the peak CK-MB value was <150 IU/liter, whereas in 39 patients it was 150 IU/liter (range 75 to 364, mean value 172; normal CK-MB is <11 IU/liter). No patient received lytic therapy.

TABLE 1

| Clinical Characteristics of Patients with Rupture | | |
|---|---|---|
| | No. (%) | Mean ISD |
| Age (yr) | | |
| Men | 47 (67) | 68 ± 4 |
| Women | 23 (33) | 77 ± 5 |
| Prior hypertension | 45 (65) | |
| Prior infarction | 13 (18) | |
| Prior CHF | 2 (3) | |
| ≦150 IU/liter CK-MB | 31 (44) | |
| ≧150 IU/liter | 39 (56) | |

CHF = congestive heart failure; CK-MB = creatine kinase, MB fraction

Electrocardiographic Site of Infarction

Figure 1:
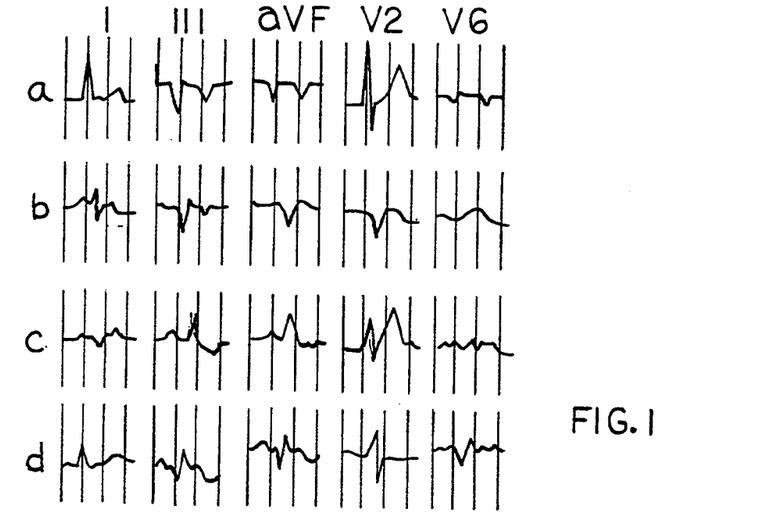
FIGS. 1A, 1B, 1C and 1D are ECG diagrams of several patients showing the ST and T wave predictive symptoms of the present invention.

Twenty patients had an acute anterior, anterolateral or anterolaterosuperior infarction, and one patient had a strictly posterior infarction as shown in Table 2 below. There was no instance of free wall rupture when the ECG changes of infarction were confined to leads $V_1$ and $V_2$. The anterior wall adjacent to the septum did rupture on 18 occasions but always when the ECG showed changes in at least leads $V_3$ and $V_4$, as well as leads $V_1$ and $V_2$. An isolated inferior infarction occurred in only three patients, whereas in 27 other patients with an inferior infarction there was involvement of the adjacent lateral or posterior wall, or both. Twenty patients had a lateral or inferolateral infarction with precordial ST-T wave changes indicative of an associated posterior process, often initially mimicking anterior subendocardial ischemia or injury. The first ECG typically showed early recognizable changes of an inferior or lateral infarction, or both, with horizontal or slightly downsloping ST segment depression in leads $V_1$ to $V_3$, followed by a totally or terminally upright T wave. Subsequent ECGs disclosed the development of abnormal R waves in leads $V_1$ to $V_3$ and an upright T wave in leads $V_2$ to $V_3$, indicative of an evolving transmural posterior, not a non-Q wave anterior, infarction as shown in FIG. 1A. Thus, 20 (29%) of the 70 patients with rupture had a posterolateral or inferoposterolaterai infarction, the latter being the single most common predecessor of rupture. Fifty-five patients (79%) had multisegment infarcts. Among them there was a midlateral or high lateral component in 48 instances (88%).

TABLE 2

| Clinical Comparison of Groups With and Without Cardiac Rupture | | | |
|---|---|---|---|
| | AMI With Rupture (n = 70) | AMI Without Rupture (n = 100) | p Value |
| Location of AMI | | | |
| Anterior | 10 (14) | 22 (22) | NS |
| Anterolateral | 6 (9) | 10 (10) | NS |
| Anterolaterosuperior | 4 (6) | 8 (8) | NS |
| Anterosuperior | 2 (3) | 2 (2) | NS |
| Inferior | 3 (4) | 26 (26) | ≦0.002 |
| Inferoposterior | 6 (9) | 16 (16) | ≦0.01 |
| Inferolateral | 9 (13) | 2 (2) | ≦0.01 |
| Inferoposterolateral | 12 (17) | 2 (2) | ≦0.02 |
| Superior (high lateral) | 2 (3) | 1 (1) | NS |
| Lateral | 1 (1) | 2 (2) | NS |
| Superolateral | 1 (1) | 1 (1) | NS |
| Posterior | 1 (1) | 2 (2) | NS |
| Posterolateral | 8 (12) | 3 (3) | ≦0.01 |
| Posterosuperior | 2 (3) | 1 (1) | NS |
| Posterosuperolateral | 3 (4) | 2 (2) | NS |
| ECG predictors | | | |
| Persistent, progressive or recurrent ST elevation | 43 (64) | 22 (22) | ≦0.002 |
| Failure of T wave to invert or reversal of inverted T waves | 66 (94) | 34 (34) | ≦0.002 |

Data are expressed as number (no.) of patients. AMI = acute myocardial infarction; ECG = electrocardiographic.

FIGS. 1A–1D show four electrocardiograms (EGGs), each recorded 48 hours after the onset of inferopostero- lateral infarction of four different patients. FIG. 1A shows the T wave pattern expected 48 hours after an inferoposterolateral infarction in a patient from the comparison group without free wall rupture. There is concordant Q wave (or R wave in lead $V_2$) development and T wave inversion in the inferior and lateral leads with an upright T wave in the posterior lead ($V_2$). FIGS. 1B–1D were recorded from three patients who had free wall rupture 1 to 3 days after the onset of infarction. In FIG. 1B, T waves are persistently positive in all three regions. At autopsy 2 days later there was fibinous pericarditis over the inferior, posterior and lateral walls, with rupture of the basal-inferior segment. In FIG. 1C the T wave has inverted in the inferior leads and in lead $V_2$ (i.e., become tall and peaked) but is persistently positive in lead $V_6$. Death occurred 3 days later. Autopsy disclosed pericarditis over and rupture of the midlateral wall. FIG. 1D shows the expected T wave inversion in the inferior leads, but the T wave has remained isoelectric in lead $V_2$, when it should have become more peaked (see FIG. 1A), and is persistently positive in the lateral lead ($V_6$), illustrating the regional specificity of the T wave changes. Autopsy the following day revealed rupture of the midlateral wall and fibrinous pericarditis and subepicardial hemorrhage overlying the posterior and lateral walls. Note the similarity of the QRS complex and ST-T wave changes in lead $V_6$ in FIGS. 1B–1D. Lead $V_7$ had a comparable appearance.

Symptoms

Symptoms, distinct from the initial chest pain and the associated symptoms of acute myocardial infarctions, occurred in all patients with rupture. (See the Venn diagrams of FIGS. 2A and 2B, wherein 2A is for rupture patients and 2B is for nonrupture patients and A=pericarditis, B=repetitive unprovoked emesis, C=restlessness and agitation.) As shown, 57 patients (81%) had positional or pleuritic chest pain, 34 without a rub, which was usually recurrent over several days often despite nonsteroid anti-inflammatory drugs. Ten of the 13 patients without positional or pleuritic pain had recurrent, uncharacterized chest pain. One of the three remaining patients had incessant restlessness and agitation, which may have obscured chest pain. Forty-five patients (64%) also had repetitive, large volume, apparently unprovoked emeses, without preceding nausea and unrelated to chest pain or medications, >24 hours after the onset of infarction. These emeses began >24 hours after admission, usually persisted for 12 to 24 hours but then stopped and did not return unless shortly before death. Four other patients had a single, large volume, unprovoked emesis, yielding a total of 49 patients with at least one large volume unprovoked emesis. Thirty-six patients (52%) had unexplained restlessness or agitation unrelated to pain, requiring the use of intravenous or intramuscular sedatives or tranquilizers. Restlessness and agitation once present continued until death. Fifty-nine (84%) of the 70 patients had at least two of the triad of symptoms, and 15 (21%) of the 70 had all three symptoms.

Among the 30 patients with an inferior infarction, the 3 with an isolated inferior infarction each had pericarditis and atypical T wave evolution at 48 hours (see later); 1 developed abrupt hypotension and bradycardia 6 hours before death, and the other 2 had significant conduction problems (sinoatrial arrest and complete heart block) requiring pacing. Thus, rupture did not occur in any patient with an uncomplicated isolated inferior infarction.

ST-T Wave Changes

A deviation of the ST segment or T wave, or both, from the expected evolutionary pattern during the first 72 hours after acute transmural myocardial infarction was observed in each patient. Forty-three (61%) of 70 patients had persistent ($\geq 3$ mm), progressive or recurrent ST segment elevation in the absence of recurrent ischemic chest pain and without re-elevation of the CK-MB. In most instances, the ST segment elevation did not recede as expected over the first 24 to 48 hours. Instead, ST segment elevation persisted or progressively increased in 23 patients. In 20 patients the ST segment returned toward the isoelectric line and then became re-elevated, whereas the remaining 27 patients (39%) it returned toward and remained at or near the isoelectric line, conforming to the expected evolutionary pattern.

Characteristic evolutionary T wave changes also failed to occur in 66 (94%) of 70 patients (Table 2). The T wave remained persistently positive during the first 48 to 72 hours after admission in 44 patients (63%), whereas in 22 other patients (31%), initial T wave inversion was followed by gradual reversal. Failure of the T wave to invert occurred in all leads that initially displayed ST segment elevation when the infarct was confined to a single region (for example, anterior).

However, when several regions were involved (for example, inferior, posterior and lateral), the T waves sometimes failed to invert concordantly in all leads that initially displayed ST segment elevation (FIG. 1B); rather, they inverted discordantly (that is, normally in one region but not in others) (FIGS. 1C and 1D). Most notably, T wave inversion did not occur in the lateral leads; but the expected inversion developed in the adjacent inferior or posterior leads, or both (FIGS. 1C and 1D). These regional T wave alterations are due to pericarditis (see later) and indicated the site of rupture in 98% of patients.

Abrupt, transient hypotension and bradycardia. Fifteen patients (21%) had an abrupt, transient episode of hypotension associated with either absolute or relative bradycardia. The hypotension was always more profound than the bradycardia and resulted in a transient preterminal appearance in each case, often associated with cyanosis or some degree of obtundation, or both. A complete, sudden loss of consciousness, occurred in five instances. Chest pain was absent or minimal. The bradycardia was sinus in 12 patients and junctional in 3. Heart block was not observed. The ventricular rate varied between 40 and 70 beats/min and in 7 patients was in the range of 60 to 70 beats/min; thus representing a relative bradycardia in comparison with the faster heart rate during the preceding minutes. The heart rate responded consistently and quickly to atropine, but the hypotension resolved more slowly over 10 minutes to 2 days. The episode of abrupt hypotension and bradycardia preceded death by 20 minutes to 3 days.

Pathologic and Surgical Observations

Figure 3A:
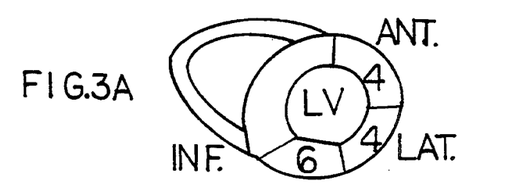
FIGS. 3A, 3B and 3C show the infarct sites associated with postinfarction rupture of the left ventricular free wall.
Figure 3B:
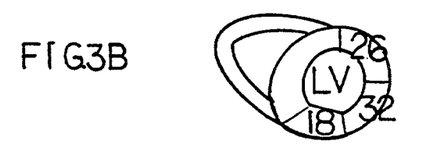
Figure 3C:
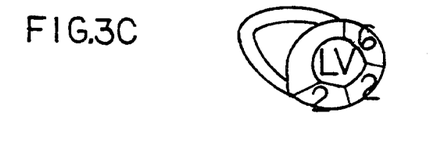

Autopsy (68 patients) or operation (2 patients) was performed in each case. Varying amounts (75 to 650 ml) of clotted and unclotted blood were found in the pericardial sac. Bleeding along the rupture tract was consistently present, whereas some degree of additional intramyocardial and subepicardial hemorrhage existed in 42% and 94%, respectively. Pericarditis was present in 69 patients (99%) and was regional in all except 3. The tear was consistently within the infarct area, usually eccentric rather than central in position and often (67% of patients) near the junction of necrotic and viable myocardium. The site of rupture was midlateral (22 patients, 32%), midanterior (18 patients 26%), midinferior (13 patients, 18%) and other (7 patients, 10%) (FIG. 3). The left circumflex coronary artery (14 patients), a dominant right coronary artery (5 patients) or the left anterior descending coronary artery (3 patients) was recently occluded in the 22 patients with a midlateral rupture and left anterior descending coronary artery in the 18 instances of midanterior rupture. Overall, the infarct-related artery was most often the left anterior descending coronary artery (29 patients, 42%), whereas the left circumflex and right coronary arteries were the culprit vessels in 35% and 23%, respectively.

FIGS. 3A–3C show the infarct sites associated with postinfarction rupture of the left ventricular free wall, basal, middle and apical, respectively, in the 70 patients, wherein ANT=anterior, CIRC=left circumflex coronary artery, INF=inferior, LAD=left anterior descending coronary artery, LAT=lateral, LV=left ventricle, and RCA=right coronary artery.

Comparison Group Data

Figure 2A:
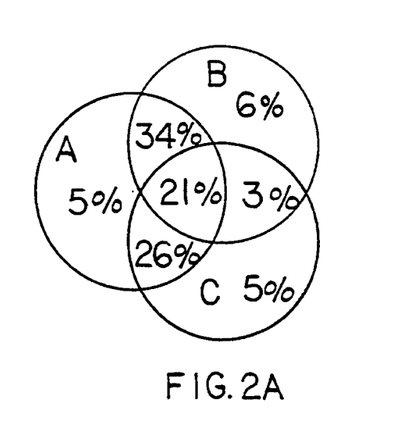
FIGS. 2A and 2B are diagrams showing the occurrence of several predictive symptoms in patients who experience cardiac rupture and patients who do not, respectively.
Figure 2B:
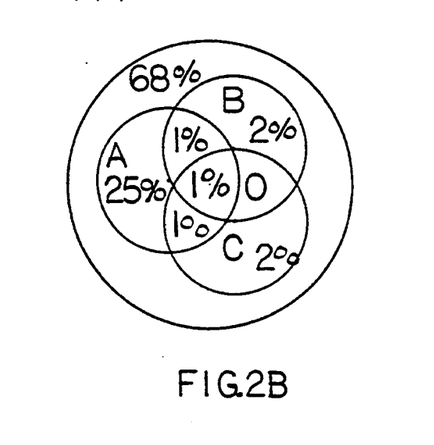

Data on the 100 comparison group patients with acute transmural infarction but without rupture are recorded in Table 2 and displayed in FIG. 2. The frequency of the three symptoms observed in the rupture group was significantly less in the comparison group, yielding sensitivities for pericarditis, repetitive emesis and restlessness and agitation of 86%, 66% and 56%, respectively, and specificities of 72%, 95% and 95% (Table 3). Two or more of the triad existed in 59 (84%) of 70 patients with rupture and in 3% of the comparison group (predictive value 95%).

In the comparison group, the T wave inverted to a depth of ≧3 mm within 48 hours if reperfusion occurred and to a depth of only 1 to 3 mm within 72 hours if reperfusion was not achieved. Deviations of the ST segment of T waves, or both, from the expected evolutionary patterns, but similar to the deviations present in the rupture group, were present in 34% of the comparison group, 85% of whom had associated pericarditis. The sensitivity, specificity and predictive value of these ECG changes, singly and together, for rupture are listed in Table 3. The T wave deviations were more sensitive but less specific than ST segment deviations.

TABLE 3

Sensitivity, Specificity and Predictive Value of Symptoms and Electrocardiographic Criteria for Cardiac Rupture

| | Sensitivity (%) | Specificity (%) | Predictive Value (%) |
|---|---|---|---|
| Pericarditis | 86 | 72 | 68 |
| Repetitive emesis | 66 | 95 | 90 |
| Restlessness, agitation | 56 | 95 | 86 |
| Two or more symptoms | 86 | 97 | 95 |
| ST segment deviations | 61 | 72 | 58 |
| T wave deviations | 94 | 66 | 66 |
| ST-T wave deviations | 61 | 68 | 64 |

DISCUSSION

Rupture of the left ventricular free wall occurs in approximately 10% of patients with fatal acute myocardial infarction and has heretofore been considered unpredictable, unpreventable and generally untreatable. Occasionally, a symptom or sign has been described at or just before the time of rupture, but no constellation of signs or symptoms, or both, indicative of impending rupture has been previously recognized. This study illustrates, however, that symptomatic, ECG and hemodynamic markers that usually permit prospective identification of the patient likely to sustain rupture.

Symptomatic Predictors

The results of this study indicate that there are three symptomatic predictors of rupture, namely, pericarditis, repetitive unprovoked emesis and restlessness and agitation. These symptoms occurred much more often in patients with rupture than in those who did not develop that complication. Pericarditis was the most common but least specific symptom portending rupture, whereas repetitive, unprovoked emesis ≧24 hours after admission and restlessness and agitation were much more specific, occurring very infrequently in patients without rupture. Moreover, all patients with rupture had at least one premonitory symptom and in 84% of patients, two or more of the triad existed, whereas only 3% of patients without rupture had two or three symptoms. Thus, several symptoms often occurred a few hours to several days before rupture and conveyed a high predictive value.

Electrocardiographic Predictors

A deviation of the ST segment or T wave, or both, from the usual evolutionary pattern after acute myocardial infarction was observed in all cases of rupture. After acute infarction, evolutionary ST-T wave changes occur in a characteristic and predictable pattern. See, Marriott, HJL. Practical Electrocardiography. Baltimore: Williams & Wilkins, 1968:238. Friedman, HH., Schamroth, L. Diagnostic Electrocardiography and Veetocardiography. New York: Hill Book, 1971:209. New The initial ST segment elevation of 1 to 5 mm or more recedes to 0 to 3 mm within 24 to 48 hours and should not recur in the absence of reinfarction, pericarditis or ventricular aneurysm. See, Zmyslinski, RW., Akiyama, T., Biddle, TL., Shah, PM. Natural Course of the ST-segment and QRS Complex in Patients with Acute Myocardial Infarction. Am. J. Cardiol. 1979; 43:29-33. Essen, RV., Merx, W., Effert, S. Spontaneous Course of ST-segment Elevation in Acute Anterior Myocardial Infarction. Circulation 1979; 49:105-11. The T wave becomes inverted within 24 to 72 h, with maximal T wave negativity always developing in the lead or leads displaying the maximal ST segment elevation initially (16).

Among patients destined to sustain rupture, persistent, progressive or recurrent ST segment elevation developed during the first 48 to 72 hours in 64% of instances in this study but in only 22% of patients who did not incur this fatal complication. Persistent or progressive ST segment elevation was somewhat more common than recurrent ST segment elevation.

A departure of the T wave from the customary course was even more frequent, occurring in 94% of instances. The T wave changes consisted of persistently positive deflections after 48 to 72 hours or gradual reversal of initially inverted T waves. The T waves changes were easier to discern than the ST segment changes because the T wave alterations were directional, whereas the ST-segment alternations were magnitudinal. Conversely, the T wave changes were beguiling because they ostensibly rendered the ECG more "normal" in appearance. Among patients with multisegment infarcts (for example, those involving the inferior, posterior and lateral walls), the T wave often inverted normally in one region but not in others. The region in which the T wave did not invert, or in which reversal of initially inverted T waves occurred, consistently corresponded with the subsequent site of rupture, often the midlateral or basal-lateral wall (29 [41%]of 70 patients).

Similar T wave alterations were found in most patients in the comparison group who developed pericarditis after infarction but who did not subsequently sustain rupture. These changes, described in detail elsewhere, developed only in those leads that initially displayed ST segment elevation and appear to be a previously unrecognized ECG manifestation of localized pericarditis after transmural myocardial infarction. Within the rupture group, it is believed that the T wave changes were due to the associated pericarditis rather than to the rupture itself because the inception of the T wave alterations coincided with the beginning of pericarditis, similar T wave alterations occurred in the comparison group with pericarditis but without rupture and the T wave changes were not present in the single patient within the rupture group without pericarditis at autopsy. Moreover, these T wave alterations were very similar to those observed experimentally by Burcheli et al. when acute myocardial infarction was accompanied by localized pericarditis in the dog model (that is, persistently upright T waves or reversal of inverted T waves). See, Burcheil, HB., Barnes, AR., Mann, FC. The Electrocardiographic Picture of Experimental Localized Pericarditis. Am. Heart J. 1939; 18:133-44.

Morphologic and Biochemical Considerations

The explanation for the minimal or absent T wave inversion or reversal of inverted T wave in both impending rupture and pericarditis after infarction without rupture may reside in morphologic changes within the subepicardial myocardium. During the first few days of pericarditis associated with various other etiologies, the ECG initially discloses ST segment elevation with upright, if not somewhat accentuated, T waves (18). These changes have been attributed to inflammation of the subepicardial myocardium (18). Hence, the hypothesis is proffered that failure of the T wave to invert, or reversal of the polarity of an inverted T wave, during the 1st 24 to 72 hours after transmural myocardial infarction may be due to subepicardial myocardial ischemia progressing to necrosis or to the slowly, outwardly advancing intramyocardial hemorrhage that often precedes rupture into the pericardial sac. See, Lewis, AJ., Burcheil, HB., Titus, JL. Clinical and Pathologic Features of Postinfarction Cardiac Ruptures. Am. J. Cardiol. 1969; 23:43-53. Lunseth, JH., Ruwaldt, M. Pathogenesis of Cardiac Rupture Due to Myocardial Infarction. Dis. Chest. 1956; 30:499-507. Sigler, LH. Sudden Death Due to Cardiac Rupture in Myocardial Ischemia and Infarction. Causes, Mechanism, and Possible Prevention. N.Y. State J. Med. 1969; 59:794-9. Inverted T waves overlying in the infarct region reflect subepicardial ischemia and are ascribed to asynchronous repolarization created by delayed repolarization within the ischemic subepicardial zone. See, Elharar, V., Zipes, D. Cardiac Electrophysiologic Alterations During Myocardial Ischemia. Am. J. Physiol. 1977; 233:H329-45. If this layer itself becomes necrotic or hemorraphagic, more synchronous repolarization may ensue, resulting in reversal of the T wave polarity.

The biochemical basis for this alternative of the T wave polarity may be considered the result of multiple factors, including, perhaps most important, the accumulation of potassium in the extracellular space from intracellular sources due to loss of subepicardial myocardial cell membrane integrity as ischemia progresses to necrosis or from hemorrhage into the subepicardial myocardium with hemolysis and hyperkalemia. Experimentally, the production of subepicardial injury by various physical and chemical stimuli, including the application of potassium, results in ST-T wave elevation. See, Hellerstein, HK., Katz, LN. The Electrical Effects of Injury at Various Myocardial Locations. Am. Heart J. 1945; 36:184-9. Furthermore, it has been observed clinically that acute hemopericardium may produce reversal of inverted T waves and even peaked T waves, presumably from potassium released by hemolyzed red blood cells. See, London, RE., London, SB. The Electrocardiographic Sign of Acute Hemopericardium. Circulation 1962; 25:780-6.

Hemodynamic Predictors

Perhaps the most dramatic indicator of impending fatal rupture identified in this study was the development of abrupt hypotension and bradycardia, often with cyanosis and loss of consciousness. Bradycardia was always mild (sometimes only relative), never due to atrioventricular block and consistently responded quickly to atropine. Blood pressure returned to normal more slowly over 10 min to 3 days. In each patient (except the two treated surgically), electro-mechanical dissociation and death ensued 20 min to 3 days later. We believe these transient episodes of hypotension and bradycardia were formes frustes of electro-mechanical dissociation and that rupture actually occurred at that time. The resultant small hemopericardium then acted as a tampon, temporarily preventing, but not ultimately averting, further egress of blood into the pericardial sac and death.

Site of Infarction and Rupture

Differing opinions exist concerning the most common site of free wall rupture. Older, smaller reports indicate the anterior wall as the most frequent site, whereas more recent, larger series have observed a preponderance of lateral and posterior wall ruptures. In this study the majority (41%) of ruptures developed through the midlateral or basal-lateral wall, a frequency similar to the 44% to 55% incidence of lateral or posterior rupture in several other reports. The significance of this observation is bolstered by the fact that only 25% of fatal and 13% of nonfatal infarctions involve the lateral wall. Thus, there appears to be a twofold to threefold increased tendency of the lateral wall to rupture. Only three instances of rupture of an isolated inferior infarction were encountered in this study, confirming a previous pathologic observation with regard to the rarity of inferior wall rupture without associated infarction of the lateral or posterior wall. See, Bjork, G., Morgensen, L., Nygquist, O., Sjorgren, A., Orinius, E. Studies of Myocardial Rupture with Cardiac Tamponade in Acute Myocardial Infarction. Chest 1972; 61:4-6.

Practical and Therapeutic Implications

It is widely believed that cardiac rupture is sudden and cannot be anticipated, hence allowing the diagnosis to be made only in the moribund patient or at autopsy. The data presented herein, and previous pathologic observations that rupture is a stuttering process characterized by progressive tears and hemorrhage within the myocardium, suggest, however, that the diagnosis can be made before death, permitting surgical intervention.

The initial ECG is of value. The presence of a lateral infarction, especially with associated inferior or posterior infarction, or both, identifies a subset of patients at increased risk for rupture. The evolution of the ST segment and T wave after 24, 48 and 72 hours have elapsed should be determined. Persistent, progressive or recurrent ST segment elevation and, especially, persistently positive T waves after 48 to 72 hours or the gradual reversal of initially inverted T waves should increase the degree of suspicion. The development of pericarditis, repetitive emeses or restlessness and agitation, particularly two or three of these symptoms, conveys predictive valve. The occurrence of abrupt hypotension and bradycardia, with an asynchronous response to atropine, warrants the performance of an echocardiogram and altering the cardiac surgery personnel. If pericardial fluid is identified by the echocardiogram, a pericardiocentesis should be performed, and if blood is obtained, immediate surgery is appropriate.

TREATMENT METHOD AND APPARATUS

Figures 4, 4A:
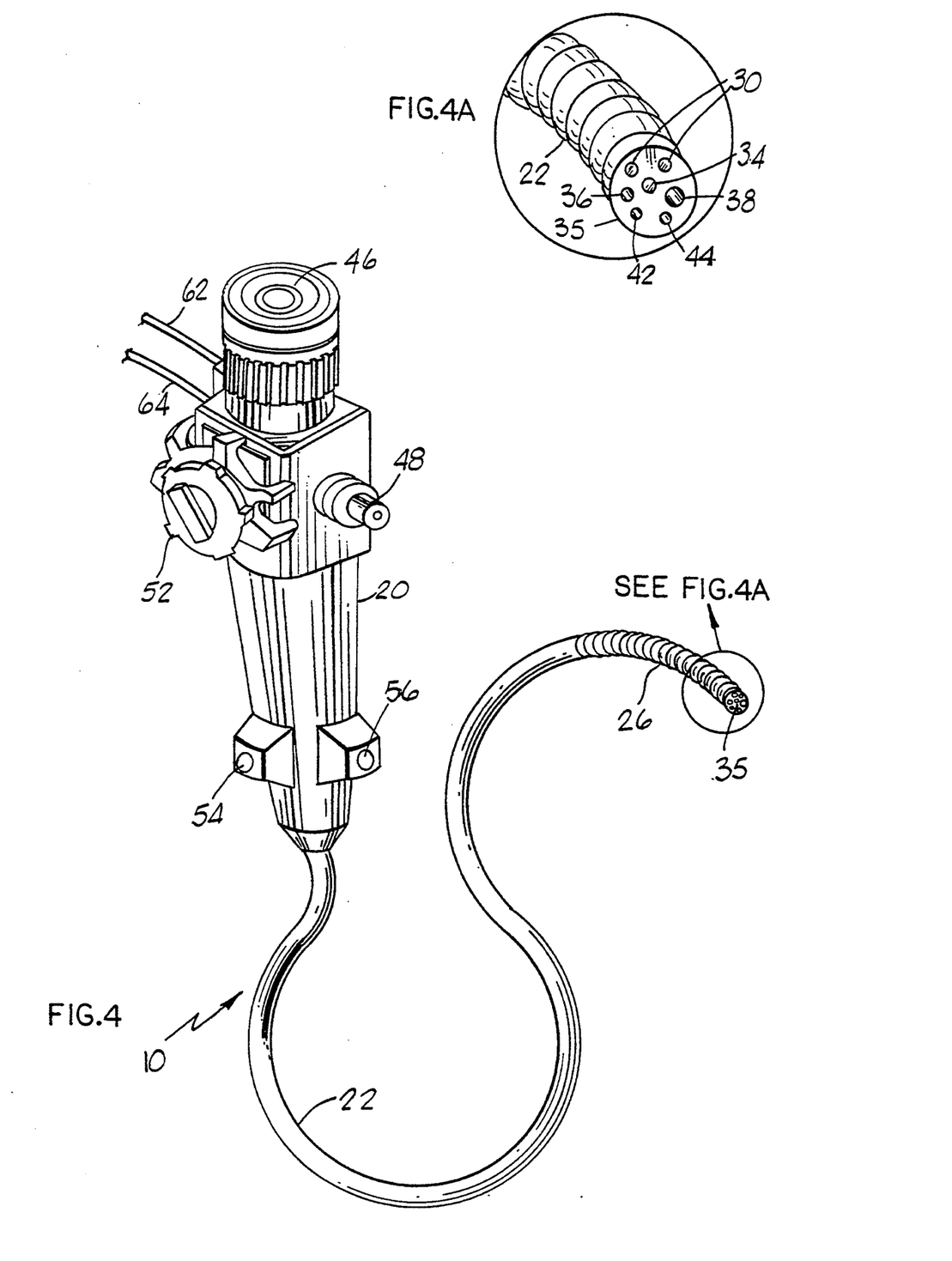
Figure 4B:
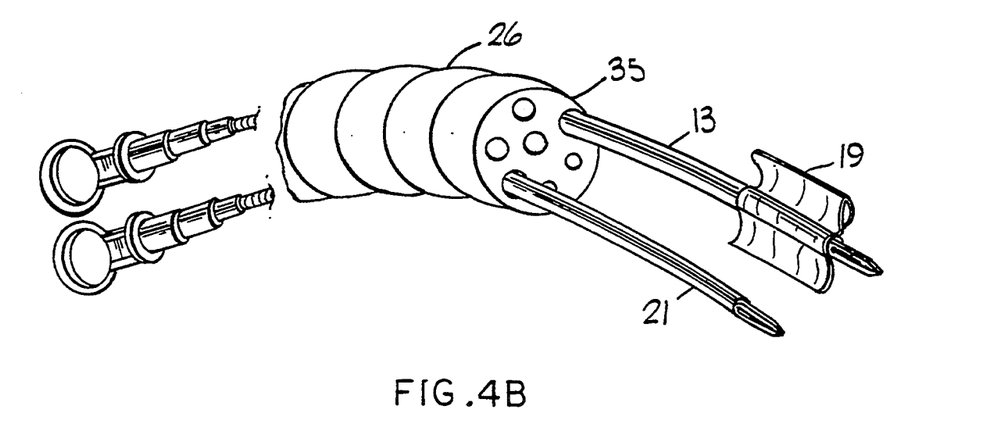
Figure 4C:
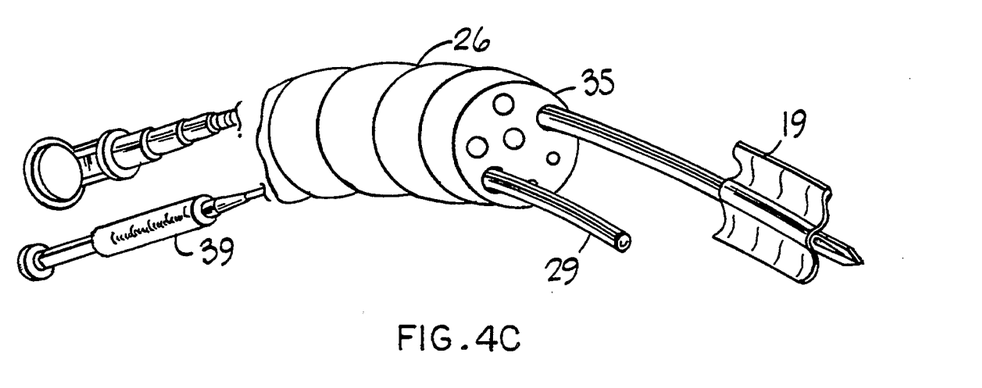

Next described is the treatment method and apparatus for patients diagnosed with an impending or existing cardiac rupture, with reference to FIGS. 4 and 4A, which show a novel surgical device 10. The device 10, which may be deemed a "pericardioscope" is somewhat similar to other manipulable endoscopes known in the art such as a gastroendoscope. In particular, the device resembles in some ways the Olympus brand model XPIO.

In a preferred embodiment, the pericardioscope 10 includes a housing 20 and a flexible section 22 having one end attached to the housing 20 and an opposite end attached to a position controllable section 26. The flexible section 22 and position controllable section 26 have several channels therethrough, as better shown in the detail view of the free end 35 of the position controllable section 26 in FIG. 4A, including at least one light source 30 (two in the embodiment shown in FIG. 4A), an object lens 34, a small instrument channel 36, a large instrument channel 38, an air insufflation channel 42 and an air desufflation channel 44. In the housing 20 is an eyepiece 46 to receive images from the object lens 34 at the free end 35 of the position controllable section 26, an air switch 48 to allow air to travel into and out of the air insufflation/desufflation channels 42 and 44, tip position controllers 52 to control the position of the position controllable section, a large instrument channel access port 54 and a small instrument channel access port 56. A fiber optic cable 62 runs from the housing 20 to a remote light source (not shown) and an air channel 64 runs from the housing to a remote pressurized air source (not shown), both of which may be housed in a single large cable. The tip position controllers 52 are of the type known in the art wherein one dial adjusts the vertical bending of the position controlled section 26 and another dial adjusts the horizontal bending. Fiberoptic devices and endoscopes are generally known in the art, and will not be described in detail here.

The large instrument channel 38 is approximately 3 mm in diameter and the small instrument channel 36 is approximately 2 mm in diameter. The light source channels 30 are of sufficient size to provide adequate illumination—generally on the order of 2 mm in diameter. The air insufflation channel 42 and air desufflation channel 44 are approximately 1 mm in diameter when using air from the remote pressurized air source at about 5-10 psi. The overall length of the flexible section 22 is about 90 cm and the length of the position controlled section 26 is about 5 cm.

Description of the Procedure

Under a local anesthetic, a sub-xyphoid incision is made. A trocar is inserted. Through the trocar, the pericardioscope is introduced and advanced to the parietal pericardium. At that point, under visual inspection of the parietal pericardium through the pericardioscope, a small incision is made with a scissors inserted through one of the two instrument channels in the pericardioscope. The pericardioscope is then advanced into the pericardial sac. It is directed toward the site of impending rupture or actual, early rupture, as predetermined by the ECG. When the tip of the pericardioscope is within 2-3 mm of the infarcted myocardium, containing the site of impending or actual, early rupture, the surface is dried by the delivery of high velocity air at body temperature with simultaneous removal of the air through an outflow port, creating isobarometric pressure within the pericardial sac. This drying technique avoids suctioning and/or applying a sponge, gauze pad or similar material to the surface of the heart, either of which could result in the removal of any protective clot overlying the site of impending or actual, early rupture. An approximately 2.5×2.5 cm square patch 19 is then inserted with a grasper 13 through the large instrument channel 38. The patch 19 is a flexible high strength woven material, preferably a mesh, such as MARLEC brand by Baird Company. The patch 19 is wrapped around the tip of the grasper 13. Upon entry into the pericardial sac, the patch 19 will naturally begin to unfurl. To facilitate that process and allow the patch 19 to lie in the same plane as and over the area of impending rupture, or actual, early rupture, another grasper 21 is inserted through the small instrument channel 36. Having access to the patch at two sites allows exact placement of the patch over the target area. To assist exact placement of the patch, a small amount of air is delivered to insufflate the local area around the patch. The surface of the heart is then again dried in the aforementioned fashion. At this point, the grasper 13 is removed from the large instrument channel 38 and a catheter 29 connected to a syringe 39 preloaded with a cyanoacrylate glue is inserted into the large instrument channel 38. The glue is injected onto the surface of the patch. The top of the catheter 29 is used to apply mild pressure onto the patch to allow very close approximation of the patch with the surface of the heart. The porous nature of the patch allows the glue to traverse the mesh work of the patch and attach it to the surface of the heart. In sequential fashion, over 1 to 2 minutes, the entire surface of the patch is attached to the target area. The patched area is then visually inspected, through the pericardioscope, for 2 to 5 minutes. The patch becomes firmly attached to the myocardium within 2 to 3 minutes, or even 30 to 60 seconds. The pericardioscope is then withdrawn and a chest tube of the same diameter left in its place. If no significant bleeding is observed within 48 hours, the chest tube is removed.

Possible Complications of the Procedure

The major potential complication of the procedure is that if an actual, early rupture has already occurred, that removal of any clotted blood from the surface of the heart may accelerate the rupturing process. It is also possible that the actual rupturing process may naturally progress as the procedure is being done. For both of these reasons, the procedure should be done only with cardiopulmonary bypass standby support. If slow bleeding occurs, it may be possible to stop it by quickly inserting the patch and glue. The glue, itself, is a sealant and should provide coagulative properties. If brisk bleeding is encountered, cardiopulmonary bypass should immediately be established and the rupture repaired by either the patch-glue technique or with stitches, or both.

Other possible complications include infection, perforation of the parietal pericardium and bleeding. It is also conceivable that the patch may detach over time. Even if the patch should detach after a period of scarring, this should be of no clinical consequence, since the soft, infarcted myocardium, which is the substrate for the impending or actual, early rupture, will have been replaced by strong, fibrous scar tissue by that time.

What is claimed is:

1. A medical treatment method for a myocardium enclosed in a pericardial sac, comprising: determining whether a patient who has experienced an acute infarction of the myocardium has at least one of pericarditis, repetitive unprovoked emesis, restlessness or agitation, a ST segment elevation or T wave pattern in an electrocardiogram that is different than normal postinfarction pattern, or abrupt hypotension and bradycardia; correlating said determination with the likelihood of a patient developing cardiac rupture; and applying and adhering a patch to the myocardium to prevent said cardiac rupture; wherein inserting the patch through a first instrument channel in a flexible endoscope from outside the patient to inside the pericardial sac.

2. The method of claim 1, wherein the endoscope further includes at least one light channel and a viewing channel, and wherein the step of inserting the patch includes wrapping it around a flexible inserter, inserting one end of the inserter with the wrapped patch through the first instrument channel and unwrapping it from the inserter within the pericardial sac.

3. The method of claim 2, wherein the inserter is a first grasper with first grasper grasping jaws on the end inserted into the first instrument channel, wherein the endoscope further includes a second instrument channel, wherein a second grasper with second grasped grasping jaws on one end is inserted into the second instrument channel, and further comprising unfurling the patch within the pericardial sac using the first grasper and second grasper.

4. The method of claim 1, wherein the endoscope includes an air insufflation channel and an air desufflation channel, and further comprising flowing air out of one of the air insufflation channel and air desufflation channel and onto the myocardium and off of the myocardium and into the other of the air insufflation channel and air desufflation channel, in order to dry a surface of the myocardium for application of said patch.

5. The method of claim 4, further comprising producing an air pocket in the pericardial sac using the air insufflation channel and air desufflation channel.

6. The method of claim 1, further comprising adhering the patch to the myocardium with a cyanoacrylate glue.

7. The method of claim 6, further comprising applying the cyanoacrylate glue by inserting a catheter through one of the first instrument channel and second instrument channel, and flowing the cyanoacrylate glue through said catheter into the pericardial sac onto the myocardium.

8. The method of claim 7, wherein the patch is a mesh material, and the patch is adhered to the myocardium by applying it to the myocardium and then applying the cyanoacrylate glue over it so that the glue flows through the mesh and onto the myocardium.

9. The method of claim 1, further comprising determining a site of an anticipated cardiac rupture based on the ST segment elevation or T wave pattern.

* * * * *